United States Patent
Lyn et al.

(10) Patent No.: US 9,011,891 B2
(45) Date of Patent: Apr. 21, 2015

(54) WATER DISPERSIBLE FORMULATION FOR DELIVERY OF BIOCONTROL FUNGI TO REDUCE AFLATOXIN

(75) Inventors: Margaret Lyn, Leland, MS (US); Hamed K. Abbas, Greenville, MS (US); Robert Zablotowicz, Cleveland, MS (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 1284 days.

(21) Appl. No.: 11/848,866

(22) Filed: Aug. 31, 2007

(65) Prior Publication Data

US 2009/0060965 A1    Mar. 5, 2009

(51) Int. Cl.
| | | |
|---|---|---|
| *A01N 25/00* | (2006.01) | |
| *A01N 25/08* | (2006.01) | |
| *A01N 25/32* | (2006.01) | |
| *A01N 63/00* | (2006.01) | |
| *A01N 63/04* | (2006.01) | |
| *A01N 65/00* | (2009.01) | |
| *A23B 9/26* | (2006.01) | |

(52) U.S. Cl.
CPC .. *A23B 9/26* (2013.01); *A01N 63/04* (2013.01)

(58) Field of Classification Search
CPC ....... A01N 63/04; A01N 43/90; A01N 51/00; A01N 2300/00; A01N 43/54; A01N 43/36; A01N 25/00; A01N 63/02; A01N 25/08; A01N 25/10; A01N 25/14; A01N 25/24; A23B 9/26; A01C 1/06; C07K 16/00; C07K 2317/14
See application file for complete search history.

(56) References Cited

U.S. PATENT DOCUMENTS

| | | | |
|---|---|---|---|
| 6,027,724 A * | 2/2000 | Dorner et al. | 424/93.5 |
| 6,884,756 B2 * | 4/2005 | Lynch et al. | 504/101 |
| 7,361,499 B1 * | 4/2008 | Abbas et al. | 435/256.1 |
| 7,789,932 B2 * | 9/2010 | Anderson et al. | 71/34 |
| 2006/0084574 A1 * | 4/2006 | Bailey et al. | 504/117 |

OTHER PUBLICATIONS

Abbas, H., et al., "Biocontrol of Aflatoxin in Corn by Inoculation with Non-Aflatoxigenic *Aspergillus flavus* Isolates", *Biocontrol Science and Technology*, vol. 16, (5), 2006, pp. 437-449.

Betran, F., et al., "Aflatoxin Accumulation in Maize Hybrids of Different Maturities," *Agronomy J.*, vol. 96, 2004, pp. 565-570.

Brown, R., et al., "Reduction in Aflatoxin Content of Maize by Atoxigenic strains of *Aspergillus flavus*," *J. of Food Protection*, vol. 54, (8), 1991, pp. 623-626.

Cotty, P., "Influence of Field Application of an Atoxigenic Strain of *Aspergillus flavus* on the Populations of *A. flavus* Infecting Cotton Bolls and on the Aflatoxin Content of Cottonseed," *Phytopathology*, vol. 84, (11), 1994, pp. 1270-1277.

Dorner, J., "Biological Control of Aflatoxin Contamination of Crops," *J. of Toxicology*, vol. 23, (2 & 3), 2004, pp. 425-450.

Dorner, J., et al., "Aflatoxin Reduction in Corn Through Field Application of Competitive Fungi," *J. Food Protection*, vol. 62, (6), 1999, pp. 650-656.

Dorner, J., et al., "Use of a Biocompetitive Agent to Control Preharvest Aflatoxin in Drought Stressed Peanuts," *J. of Food Protection*, vol. 55, (11), 1992, pp. 888-892.

Windhan, G., et al., "Inoculation Techniques Used to Quantify Aflatoxin Resistance in Corn," *J. of Toxicology*, vol. 22, (2 & 3), 2003, pp. 313-325.

* cited by examiner

*Primary Examiner* — Debbie K Ware
(74) *Attorney, Agent, or Firm* — John D. Fado; Evelyn M. Rabin

(57) ABSTRACT

A formulation containing conidia of non-toxic strains of fungi is a useful biocontrol agent for preventing toxin contamination in agricultural commodities, especially those for human and animal consumption such as peanuts, corn, cotton and tree nuts. The formulation of the invention is a water dispersible granule formulation suitable for spraying and includes non-toxigenic and/or non-aflatoxigenic *Aspergillus flavus* strains capable of inhibiting growth of fungi which produce aflatoxin and further capable of suppressing production of aflatoxin by the toxigenic fungi. A method of preparing the formulation is shown.

31 Claims, No Drawings

WATER DISPERSIBLE FORMULATION FOR DELIVERY OF BIOCONTROL FUNGI TO REDUCE AFLATOXIN

BACKGROUND OF THE INVENTION

1. Field of the Invention

This invention relates to a water dispersible granule formulation containing biocontrol agents for the reduction of aflatoxin contamination in food and feed commodities, in particular corn, and a method of preparing the formulation. The water dispersible granule formulation comprises biocontrol agents embedded in a granular matrix which is dispersible upon the addition of an aqueous solvent. The biocontrol agents are non-toxigenic and non-aflatoxigenic *Aspergillus flavus* strains which are capable of inhibiting colonization by aflatoxin-producing fungi and which are further capable of suppressing production of aflatoxin by the toxigenic fungi. The water dispersible granule formulation of the invention exhibits a high degree of stability under storage and field conditions.

2. Description of the Relevant Art

Many fungi produce secondary metabolites that are not necessary for their growth or reproduction. When toxic to humans or livestock, these metabolites are classified as mycotoxins. Four of the more important mycotoxin-producing fungal genera are *Aspergillus, Fusarium, Penicillium*, and *Alternaria* (Council for Agricultural Science and Technology [CAST]. 2003. *Task Force Report* 139, Ames, Iowa). These fungi produce mycotoxins that could adversely affect the quality and supply of various food and feed commodities including corn, cottonseed, cereal grains, peanuts, and tree nuts.

Mycotoxins are estimated to cost the United States and Canadian feed and livestock-industries an overall loss of five billion annually: aflatoxin, a class of mycotoxins produced by *Aspergillus* spp., is of the greatest concern (Robbens and Cardwell. 2005. In: *Aflatoxin and Food Safety*, Abbas, H. K (Ed.), CRC Press, Boca Raton, Fla., pp. 1-12) The two major mycotoxins prevalent as contaminants in food and feed produced by *A. flavus* are aflatoxins B1 and B2 (Payne, G. S. 1992. *Critical Rev. Plant Sci.* 10: 423-440). Aflatoxin $B_1$ ($AFB_1$) is regarded as the most potent and prevalent (International Agency for Research on Cancer-World Health Organization [IRAC-WHO]. 1993. In: *IARC Monographs on tho Evaluation of Carcinogenic Risks to Humans*, Lyon, France, pp. 56, 467-488). Incidences of contamination are most frequently linked to *A. flavus* (Diener et al. 1987. *Ann. Rev. Phytopath.* 25: 249-270). This fungus-is capable of growing over a wide temperature range, namely 10° C.-43° C. and a wide water activity range (0.82-0.998) (Food and Agriculture Organization of the United Nations/International Atomic Energy Agency [FAO/IAEA]. 2001. In: *FAO Food and Nutrition Paper*, FAO. Rome, Italy, pp. 73, 75-93). However, drought conditions, mechanical injury, or pest damage generally exacerbates preharvest aflatoxin contamination in corn.

The current maximum aflatoxin level permissible in human food and animal feed is 20 µg/kg (CAST, supra; van Egmond and Jonker. 2004. *J. Toxicol.—Toxin Rev.* 23: 273-293). Although mycotoxins on agricultural commodities are unavoidable, the level of these contaminants may be controlled with good agronomic practices. Several preharvest aflatoxin management strategies have been proposed (Betran and Isakeit. 2004. *Agron. J.* 96: 565-570) with varying degrees of success. One promising control strategy is biological control using non-toxigenic *A. flavus* (Dorner, J. W. 2004. *J. Toxicol.—Toxin Rev.* 23: 425-450). Brown et al. (1991. *J. Food Protect.* 54: 623-626) demonstrated that aflatoxin levels could be suppressed by direct wounding and injection of corn ears with a non-toxigenic strain of *A. flavus*. In contrast to the direct, mechanical delivery strategy of Brown et al., an indirect delivery to soil is more routinely used. Here, the soil inoculum is typically an aggressive, non-toxigenic strain of *A. flavus*, which is initially cultured on cereal grains. These grains serve as a nutrient source for proliferation of the biocontrol *A. flavus* strain and are applied as soil treatments to target crops. While on the grains, the non-toxigenic strain sporulates profusely, disperses by wind or water, and competes with endemic aflatoxigenic strains for resources, collectively resulting in a reduction of aflatoxin levels. This soil treatment strategy has been successful in peanuts (Dorner et al. 1992. *J. Food Protect.* 55: 888-892), cotton (Cotty, P. J. 1994. *Phytopath.* 84: 1270-1277) and corn (Dorner et al. 1999. *J. Food Protection* 62: 650-656). A similar strategy using a soil-applied inoculation was implemented for Mississippi Delta corn production (Abbas et al. 2006. *Biocontrol Sci. Tech.* 16: 437-449). The Mississippi Delta corn study identified K49, a non-toxigenic strain of *A. flavus* that exhibited both significant reduction of aflatoxin contamination in four years of field trials and good colonization potential.

Despite the success of the above treatment strategies, there are associated limitations in reduction to practice in a commercial agricultural setting. Consequently, there remains a need to develop a direct aerial delivery approach to effectively mitigate aflatoxin contamination in preharvest corn and to alleviate application dependency on optimal environmental conditions.

SUMMARY OF THE INVENTION

We have developed a composition which is a water dispersible granule formulation containing biocontrol agents which can be applied as a sprayable conidial suspension for the prevention of aflatoxin contamination in food and feed and a method for preparing the water dispersible granule formulation.

In accordance with this discovery, it is an object of the invention to provide a water dispersible granule formulation containing isolated non-aflatoxigenic and non-toxigenic *A. flavus* strains which can act as biocontrol agents and inhibit the proliferation of aflatoxin-producing fungi thus preventing aflatoxin contamination in food and feed. In the preferred embodiments of the invention, the non-toxigenic strain designated as K49 is provided.

It is also an object of the invention to formulate biocontrol agents without loss of viability and with a high degree of stability under storage and field conditions Another object of the invention is to prepare biocontrol products that are clean, easy to handle, and have relatively low crop phytotoxicity.

A further object of the invention is to package biocontrol agents into formulations that can be applied with conventional agricultural sprayers.

Other objects and advantages of this invention will become readily apparent from the ensuing description.

DETAILED DESCRIPTION OF THE INVENTION

We have developed a preparation method for a water dispersible granule formulation containing a non-toxigenic biocontrol *A. flavus* strain. Formulated and unformulated inoculation of non-toxigenic strain K49 was compared with soil inoculation to determine the effects on colonization potential and aflatoxin levels in field corn. The comparison was conducted to evaluate the direct delivery approach to mitigate aflatoxin contamination in pre-harvest corn. Similar levels of colonization and reduction in aflatoxin are found when spray applications of formulated and unformulated conidia are compared. The significance of this finding is that a suitable biological control product that uses conventional application technologies can be developed to mitigate aflatoxin contamination in corn. The excellent reduction in aflatoxin levels and apparent establishment of the biocontrol strain supports the hypothesis that the most effective method for reducing aflatoxin contamination on corn may be a direct application of the biocontrol agent to aflatoxin-susceptible or reproductive organs of corn.

The method of adding highly competitive, non-toxigenic strains of *A. flavus* to soil has been routinely used and has resulted in lower concentrations of toxins in agricultural crops due to the non-toxigenic strains of *Aspergillus* becoming biocompetitive with the soil microflora and preventing the buildup of toxin-producing strains that normally occurs during late-season drought. Through competitive displacement, the toxigenic strains of fungi found naturally in soil are replaced by non-toxigenic or non-aflatoxigenic strains added to the soil. Therefore, any crops subjected to late-season drought stress are invaded predominately by the biocompetitive strains which are unable to produce toxins.

However, the use of cereal grain inoculants to control aflatoxin in corn poses drawbacks such as 1) application of a solid matrix may be difficult for commercial use when the crop is at later stages of ontogeny, 2) certain biotic, abiotic, and weather factors can limit or delay conidia dispersal from granular point sources to aerial regions of corn, and 3) ongoing sporulation on the applied grains in the field may raise health and safety issues. Ultimately, the success of a biological control approach is governed by the dynamics or biological competition between *A. flavus* communities. Both formulated and unformulated conidia of K49 were applied to corn reproductive tissues and their effects on aflatoxin levels were compared. When directly sprayed to corn ears, both formulated and unformulated conidia were highly effective in reducing aflatoxin contamination in corn. Although the formulated material was prepared and stored for eleven months, no difference in efficacy was found between the formulated and unformulated material which consisted of freshly harvested conidia. As application of freshly generated biocontrol agents is unlikely to be a commercially feasible option, a stable formulation capable of effectively delivering biocontrol agents provides an important and commercially feasible option for controlling aflatoxin in corn and other crops susceptible to mycotoxin contamination. The concentration of the material used for application also differed. Formulated material in this study was applied at 9 kg/ha; whereas, grain-based soil inoculants were routinely applied at rates from 20 to 200 kg/ha (Abbas et al. 2006; Cotty; Dorner et al. 1998: supra). Further optimization of the formulation described herein as well as the methodology involved in the spray application may further reduce the amount of formulation required per unit area to control aflatoxin in corn.

The method of the invention is applicable to any agricultural commodity which is grown for human consumption and/or animal feed and/or which is damaged by fungal toxins and which can benefit from direct application to targeted sites on the plant, such as for example, corn, cotton, tree nuts, and olives.

For purposes of this invention, a fungal preparation or fungal agricultural biocontrol composition refers to a microbial preparation wherein the microbes comprise, consist essentially of, or consist of non-toxigenic or non-aflatoxigenic strains of *Aspergillus*. The fungal formulated preparations may contain one or more non-toxigenic strains or non-aflatoxigenic strains of *Aspergillus*. Non-toxigenic strains of *Aspergillus* include any strain which does not produce either aflatoxin or cyclopiazonic acid (CPA). Non-aflatoxigenic strains of *Aspergillus* include any strain which does not produce the toxin aflatoxin, but which continues to produce cyclopiazonic acid (CPA). The agricultural biocontrol composition for purposes of this invention includes a non-toxigenic strain or strains of fungi, or a non-aflatoxigenic strain or strains of fungi, embedded within agriculturally acceptable carriers which may be any carrier to which the fungi can be attached and are not harmful to the fungi or crops which are treated with the composition. An example of a non-toxigenic strain includes *A. flavus* K49. The fungi especially useful in the present invention are strains possessing the identifying characteristics of non-toxigenic *A. flavus* K49, designated NRRL 30797. These characteristics are the inability to produce the toxins aflatoxin and CPA and the ability to be biocompetitive when applied to soils growing agricultural commodities. An example of a non-aflatoxigenic strain includes *A. flavus* CT3. The fungi which are also especially useful in the present invention are strains possessing the identifying characteristics of the non-aflatoxigenic *A. flavus* strain CT3, designated NRRL 30798. These characteristics are the inability to produce aflatoxin and the ability to be biocompetitive when applied to soils growing agricultural commodities.

When non-toxigenic and non-aflatoxigenic strains of *Aspergillus* are cultured as single strains on granular food sources, such as for example wheat, rice, rye, etc., these fed sources, when they are fully colonized, contain approximately $10^8$ colony forming units (CFU) of fungi per gram of food source. For these granular food sources, inoculated grains are incubated at about 35° C. After 24 h growth, the inoculated wheat was manually shaken and incubated for another 24 h and further homogenized by manual shaking. Colonization by the inoculant strain was confirmed by determining aflatoxins concentration in inoculants. The inoculated product can be stored at about 5° C. for approximately 2 months or longer if dried below a critical water content.

The non-toxigenic and non-aflatoxigenic strains of *Aspergillus* are applied to plants in amounts effective to reduce toxin levels in agricultural commodities. As used herein "reduce toxin levels" refers to a reduction in amounts of toxin compared to that which would be expected in agricultural commodities which were not treated according to the methods of the present invention. Any accurate method of measuring and comparing toxin levels may be used for such comparisons, as would be apparent to those skilled in the art.

As used herein "in amounts effective", "an amount effective" or "an effective amount" refer to the amount of the fungal preparation administered wherein the effect of the administration acts to reduce toxin contamination of agricultural commodities.

EXAMPLES

Having now generally described this invention, the same will be better understood by reference to certain specific examples, which are included herein only to further illustrate the invention and are not intended to limit the scope of the invention as defined by the claims.

Example 1

*Aspergillus flavus* Strains

Non-toxigenic *A. flavus* strain K49 (NRRL 30797) and the aflatoxigenic strain F3W4 (NRRL 30796) were maintained on silica gel at 4° C., and were verified for appropriate phenotypic characteristics, aflatoxin profile, sclerotia formation, and colony morphology and conidia formation prior to initiation of studies (Abbas et al. 2006. *Biocontrol Science and Technology* 16: 437-449).

Example 2

Formulation Materials and Water Dispersible Granule Preparation

A calcined kaolin clay with mean particle size less than 1 micron was used as a carrier in the following water dispersible granule formulation (WG). Sodium carboxymethylcellulose was used as a binder in addition to trehalose. Trehalose was utilized as a multifunctional formulant. This disaccharide was strategically included in the formulation to serve as an osmoprotectant, post-application adhesive or sticker, and potential nutrient source for K49. In particular, the composition of the dry ingredients in the formulation was: 76-90% Satintone 5HB as the carrier, 1-4% Nilyn XL 90 as the binder, and 5-20% trehalose, as the osmoprotectant, post-application adhesive and nutrient source for K49. Dry ingredients were mixed until visually homogeneous in a high shear mixer before mixing in approximately 510 mL 0.1% (w/v) peptone solution containing 5% of the total dry amount of trehalose and conidia of K49 at $4 \times 10^8$ CFUs/g of wet mixture per 500 g dry ingredients. Conidia were harvested from malt extract agar plates with small aliquots of a 0.1% peptone solution. Thus, the conidia were embedded within the formulated granules. Control granules without the *A. flavus* conidia were prepared and processed as described above.

Clays other than calcined kaolin clay can be utilized in the formulation of the invention, that is, any clay having an appropriate size, i.e., a size comparable to the size of the organism and of a size small enough to not lead to clogs in the sprayer system can be used. Thus, other possible silicate clays and clay mixtures can be used, such as, for example, bentonite, kaolinite, and smectites, including montmorillonite and beidellite.

The above mixtures were produced separately with a pan granulator (LCI Corp) equipped with either a 1.2 mm or 2.0 mm die and dried under vacuum to a water activity of approximately 0.30. The 2.0 mm and 1.2 mm granules are referred to as Product 1 and Product 2, respectively. The granules were stored at 4° C. for ~330 days during which time the survival of the *A. flavus* propagules was determined intermittently by plating on semi-selective media. Triplicate samples were homogenized in water agar (0.2% w/v) using reciprocal shaking (30 min, 100 strokes per minute), serially diluted and plated on modified rose Bengal media (MDRB; Horn and Dorner. 1998. *Mycologia* 90: 767-776).

Analysis of the conidia granule formulation immediately after drying indicated >$3 \times 10^8$ cfu/g. A relatively high level of *A. flavus* strain K49 survival was observed as no further loss of viability occurred following 11 months of storage of the formulated K49 at 4° C. (Table 1). However, only a 50% drop in viable fungal propagules was observed after 2 years of storage.

The formulated granules contain the embedded biocontrol agent, here, K49 conidia. Upon contact with water (as in Example 5) or another aqueous solution, the granules disperse or disintegrate and the biocontrol agent is released and available to function as a biocontrol agent.

TABLE 1

Survival of *A. flavus* strain K49 water dispersible granules.

|  | Product 1 (2.0 mm WG) | Product 2 (1.2 mm WG) |
|---|---|---|
|  | Colony Forming Units *A. flavus*/g | |
| After Drying | $3.12 \pm 0.35 \times 10^8$ | $3.70 \pm 0.10 \times 10^8$ |
| Storage at 4° C. for 20 d | $2.57 \pm 0.15 \times 10^8$ | $2.95 \pm 0.34 \times 10^8$ |
| Storage at 4° C. for 330 d | $3.90 \pm 0.36 \times 10^8$ | $3.18 \pm 0.21 \times 10^8$ |
| Storage at 4° C. for 745 d | $1.66 \pm 0.44 \times 10^8$ | $1.49 \pm 0.20 \times 10^8$ |

Data presented are means of three replicates ± standard deviation.

Example 3

Conidia and Solid Inoculum Preparation

For unformulated conidia inoculum production, stock cultures were transferred to 40 potato dextrose agar (PDA) plates and incubated for 5-7 days at 28° C., in 12 hr light (165 µmol/m$^2$/s$^1$) and 12 hr dark regimes. Conidia and mycelium were scraped off the plate with aqueous Tween 20 (0.2% w/v). Vegetative fungal structures were removed from the conidia suspension by filtering through two layers of cheesecloth. The density of conidia rate was determined using a hemocytometer and adjusted to a final concentration of $4.1 \times 10^6$ conidia/mL.

Wheat was used as the inoculant carrier for soil inoculation as described elsewhere (Abbas et al. 2006, supra). Wheat seed was hydrated in water overnight, drained, and autoclaved in polypropylene bags (1 kg/bag with 200 ml water) for 1 hr at 121° C. Initial inoculum of *A. flavus* were 5-day old PDA cultures, a 3 cm$^2$ section per bag and incubated at 35° C. After 48 hr at 35° C. the wheat was fully colonized. This product was then homogenized by manual shaking and stored at 4° C. until used for field trials.

Example 4

Field Colonization Pin Bar Assay

A pin bar inoculation technique (Windham et al. 2003. *J. Toxicol.—Toxin Rev.* 22: 313-325) was used to determine the relative colonization of corn by an unformulated conidial suspension of K49 compared to the WG formulation of K49 in 2005 in field trials conducted at Stoneville and Elizabeth, Miss. The glyphosate-resistant corn hybrid (Garst 8270 rr) was used in Stoneville, and a hybrid expressing the *Bacillus thuringiensis* endotoxin gene (Agrigold A6333 bt) was used in the Elizabeth trials. Corn ears were inoculated at 25 d after mid-silking (dent kernels development). Corn ears (100 per treatment) were inoculated separately with either a formulated (15 g/L) or an unformulated conidia suspension ($5 \times 10^6$ conidia/mL) at mid-silking stage using a pin bar (three 100 mm-long rows of 12 sewing needles mounted on a wood block, each with 6 mm of the points exposed). Pin bars were dipped in conidial suspensions, and the bars were pressed into the ear. At various intervals after pin-bar inoculation, ten inoculated ears were harvested per treatment, and the total number of kernels in the inoculated zone and the number of infected kernels was determined based on counting and visual assessment of fungal growth on individual kernels.

A similar final level of-colonization of corn kernels by strain K49 introduced as formulated and unformulated conidia was observed at two locations in 2005 using the pin bar inoculation assay (Table 2). The initial rate of K49 colonization of corn kernels observed at the Stoneville site (non- BT hybrid) was more rapid compared to the Elizabeth site (BT hybrid). The Stoneville test was inoculated 10 d earlier than the Elizabeth test and climatic conditions may have influenced the rate of colonization. The incidence of *A. flavus* colonization in the non-inoculated control at the Stoneville site was greater than at the Elizabeth site. This difference may be attributed to the use of BT hybrid (Elizabeth site) which lowers the incidence of the European cornborer (Dowd, B. W. 2003. *J. Toxicology—Toxin Review* 22; 327-350). At the Elizabeth location, a more rapid colonization of corn kernels was observed in ears inoculated with Product 1 compared to the non-formulated conidia at 5 and 7 days after inoculation, while at the Stoneville location both formulations elicited superior colonization compared to non-formulated conidia at 7 days after inoculation. Superior colonization of strain K49 was observed in Product 1 compared to product 2 at the Stoneville location at 5 days and at the Elizabeth location at 9 days after inoculation. There was no negative effect of formulation and formulation aging (20 d in storage) on colonization by K49 conidia and at certain early dates, colonization of formulated K49 was more aggressive than unformulated conidia. Based on these preliminary results, Product 1 (2.0 mm diameter WG) was chosen for application in the second year of field testing.

TABLE 2

Colonization of corn kernels following inoculation with K49 applied as water dispersible granules or free conidia at two locations.

| | Infected kernels (%) | | | | | |
|---|---|---|---|---|---|---|
| | Day 2 | Day 5 | Day 7 | Day 9 | Day 12 | Day 14 |
| Elizabeth (BT)* | | | | | | |
| Control | 0 | 0 c | 0.8 c | 2.1 b | 5.0 b | 7.5 b |
| Product 1 | 0 | 54.1 a | 85.7 a | 100.0 a | 100.0 a | 98.1 a |
| Product 2 | 0 | 51.1 a | 73.1 a | 97.2 a | 100.0 a | 98.1 a |
| Non-formulated conidia | 0 | 34.4 b | 67.6 b | 100.0 a | 100.0 a | 92.0 a |
| LSD (Pr > 0.05) | | 16.2 | 10.0 | 4.5 | 8.2 | 10.8 |
| Stoneville (RR)[#] | | | | | | |
| Control | 0.0 b | 0.9 c | 5.1 c | 9.4 b | 6.9 b | 23.9 b |
| Product 1 | 0.6 b | 80.1 a | 98.7 a | 93.8 a | 98.5 a | 99.2 a |
| Product 2 | 0.0 b | 37.5 b | 98.9 a | 94.5 a | 96.7 a | 93.6 a |
| Non-formulated conidia | 17.2 a | 69.7 a | 85.7 b | 91.1 a | 96.0 a | 96.6 a |
| | | 14.55 | 12.0 | 8.9 | 5.2 | 14.3 |

Mean of ten replicates sampled at each day. Values followed by the same letter do not differ significantly at the 95% confidence level.
BT = Hybrid containing the BT construct,
RR = Hybrid modified for resistance to glyphosate.

Example 5

Field Experiment Aflatoxin Control and Strain Establishment

A field study was conducted at Stoneville, Miss. in 2006 to evaluate the efficacy of foliar applications of the biological control atoxigenic strain K49 to reduce infection by aflatoxigenic isolates of *A. flavus* and reduce aflatoxin contamination. Corn (DK C69-70RR) was planted on Apr. 14, 2006 on a Dundee silt loam soil in Stoneville, Miss. An experimental design of a randomized complete block design with 6 treatments replicated in 3 blocks was used. Each experimental unit consisted of three 9.36 meter rows (1.06 m wide), with one treated row (center 25 to 30 plants) and two non-treated buffer rows. The seven treatments consisted of 1) non-treated control; 2) soil inoculated with a wheat inoculant of the aflatoxigenic *A. flavus* strain F3W4 (20 kg/ha); 3) soil inoculated with a wheat formulation of K49; 4) soil inoculated with both F3W4 and K49 wheat; 5) suspension of K49 extruded granules; and 6) suspension of spray suspension of freshly harvested K49 conidia.

On June 26 (at early silking stage), a wheat inoculant of the aflatoxigenic strain F3W4 and the atoxigenic strain K49 was applied to appropriate plats at a rate of 20 kg/ha. On June 30 (mid-silking stage), the spray inoculants (treatments 5 and 6) were applied using a hand held sprayer. The spray consisted of 56 g of formulated product suspended in 4 liter of 0.2% w/v Tween 20, applied at a rate of ~600 mL per plot. The spray was directed to the upper one third of the plants, targeting the ears. At physiological maturity (August 17), all ears in a 6 m length from center of the treated row were hand harvested, dried, shelled and ground.

The enumeration of *Aspergillus* propagule density and isolate characterization was assessed using selective media. Ground grain samples were homogenized in 0.2% w/v water agar, serially diluted and plated on MDRB agar. Colony forming units (cfu) were calculated following 5 d incubation. Thirty colonies per plot were transferred to CD-PDA (PDA with 0.3% β-cyclodextrin) and incubated for 5 d under continuous dark at 28° C., and evaluated for aflatoxin production based on colony pigmentation and color change following exposure to ammonia vapors (Abbas et al. 2004. *Canad. J. Microbiol.* 50: 193-199).

All field data, colonization assays, *Aspergillus* recovery and toxin phenotype, and aflatoxin contamination was analyzed using PROC GLM of the Statistical Analysis System (SAS. 2001. SAS® Proprietary Software Release 8.2, Windows version 5.1.2600. SAS Institute Inc. Cary, N.C.). Mean separation was performed using Fisher's Least Significant Difference.

The number of cfu of *A. flavus* recovered from ground corn ranged from log 5.4 to 6.3 propagules/g grain, with the highest recover from corn treated with an unformulated conidia spray of K49 (Table 3). This level of colonization is much higher than the *A. flavus* propagule counts found in corn in previous studies (Abbas et al. 2006, supra) where recovery ranged from 3.4 to 4.4 of log cfu/g grain. The lowest proportion (4 to 6%) of aflatoxigenic isolates was found in the formulated and unformulated spray application of K49 (Table 3). In all other treatments, a similar level of aflatoxigenic isolates (50 to 71%) was observed and was not significantly affected by soil inoculation with either the non-toxigenic strain K49 or the toxigenic strain F3W4.

TABLE 3

Recovery of *A. flavus* isolates from corn under varied inoculation treatments.

| Treatment | *A. flavus* ($log_{10}$ cfu/g) | Toxigenic isolates (%) |
|---|---|---|
| No inoculant | 5.5 bc | 69 a |
| K49 wheat inoculant | 5.7 b | 52 a |
| F3W4 wheat inoculant | 5.7 b | 71 a |
| FSW4 + K49 wheat inoculant | 5.6 bc | 50 a |
| F3W4 wheat inoculant + K49 formulated spray | 5.4 c | 4 b |
| F3W4 wheat inoculant + K49 unformulated conidia | 6.3 a | 6 b |
| LSD (Pr > 0.05 level) | 0.2 | 42 |

Mean of three replicates, values followed by the same letter do not differ significantly at the 95% confidence level.

An atoxigenic:toxigenic ratio of 24:1, 15:1, and 1:1 was determined from average cfu counts and frequency of the two phenotypes for the formulated spray, unformulated spray and all remaining treatments, respectively. Previous research indicated that K49 colonization on corn ears could be enhanced by soil inoculation (Abbas et al. 2006, supra): however, this was not observed in this study (Table 3). A possible explanation for this difference is that the soil inoculum of K49 was applied at the mid-silking stage in this study; whereas, in the earlier study, the inoculum was applied at the V6 stage of ontogeny. In studies on cotton, Cotty (supra) observed that 67% of the *A. flavus* recovered from cotton bolls were in the same vegetative compatibility group as the introduced non-toxigenic strain when applied as a soil inoculant, compared to 46%, as a spray inoculant, and 25%, in non-treated control plots. This indicated that a lower degree of establishment of the biocontrol strain was achieved by spray application in these Arizona field trials.

The low recovery level of aflatoxigenic *A. flavus* in corn that received formulated or unformulated K49 spray treatments indicates an apparent establishment, colonization and competitive displacement of toxigenic *Aspergillus* by the introduced non-toxigenic K49 strain when applied directly to the reproductive structures of corn.

Example 6

Aflatoxin Determination and *Aspergillus* Recovery

Aflatoxin concentration was quantitatively determined using commercial ELISA kits (Neogen Corp, Lansing Mich.) according to Abbas et al. (2002, 2006, supra). Triplicate sub-samples of ground corn (20 g) were extracted in 100 mL of methanol (70%) for 30 min on a high speed reciprocal shaker, and clarified by centrifugation (10 min, 8000×g), and the methanol extracts were analyzed by ELISA. The limit of detection in this assay was 5 ng/g total aflatoxin.

In these field studies, a relatively high level of aflatoxin contamination was observed from natural infection in control untreated plots and in control plots where soil was inoculated with aflatoxigenic F3W4 infested wheat. Respectively, 428 and 635 µg/kg aflatoxin were observed with a wide variance among samples for these two control treatments (Table 4). However, when a soil application of atoxigenic K49 was made as infested wheat granules to plots that were either untreated or simultaneously treated with a soil inoculation of F3W4, aflatoxin levels (educed significantly (P<0.05) to 44 and 223 µg/kg, respectively. Herein, soil applications of K49 with F3W4 resulted in a significant decrease in average aflatoxin levels (~400 µg/kg) in corn compared to corn inoculated with F3W4 alone. However, levels of aflatoxin in corn inoculated with K49 and F3W4 infected grain was not significantly different from the untreated controls.

TABLE 4

Aflatoxin levels in corn as affected by various inoculation treatments.

| Treatment | Aflatoxin concentration (µg/kg) |
| --- | --- |
| No inoculant | 428 ab |
| K49 wheat inoculant | 44 c |
| F3W4 wheat inoculant | 635 a |
| F3W4 + K49 wheat inoculant | 223 bc |
| F3W4 wheat inoculant + K49 formulated spray | 18 c |
| F3W4 wheat inoculant + K49 unformulated conidia | 21 c |
| LSD (Pr > 0.05 level) | 287 |

Mean of three replicates, values followed by the same letter do not differ significantly at the 95% confidence level.

In previous studies where K49 was introduced as a soil application, corn aflatoxin contamination reduced by 58 to 76% relative to untreated plots when there was an abundant natural aflatoxin incidence (Abbas of al. 2006, supra). When the soil was inoculated with the aflatoxigenic isolate F3W4, co-inoculation with K49 on wheat reduced aflatoxin contamination by 74 to 95% relative to aflatoxin concentrations in plots where the soil was inoculated with F3W4 alone. In other studies, aflatoxin was reduced by 66 and 87% for two consecutive years in corn plots treated with equal mixtures of rice colonized by two different non-aflatoxigenic *Aspergillus* species relative to aflatoxin levels in untreated corn plots (Dorner et al. 1999, supra). In terms of percent aflatoxins reduction, our results of 90 and 65% are consistent with earlier studies. While soil applications of K49 elicited a significant reduction in aflatoxin contamination, aflatoxin concentrations remained above regulatory limits for use of corn as food or feed stock.

Spray treatments of corn with either formulated or unformulated K49 conidial suspensions in plots where the soil had been infested with aflatoxigenic F3W4, resulted in ~615 µg/kg reduction in average aflatoxin concentration. Specifically, direct application of either formulated or unformulated K49 to reproductive corn structures in F3W4 soil-spiked plots significantly (P<0.05) reduced aflatoxin levels to 18 and 21 µg/kg, respectively, in comparison to a 635 µg/kg aflatoxin level found in the control plot that received only the soil F3W4 application. Thus, greater than 97% reduction in average aflatoxin concentration is attributed to spray inoculations with K49 in contrast to 65% from indirect soil application of K49. In cotton, a grain application reduced aflatoxin contamination by 75% while no effect was observed when the non-aflatoxigenic strain was applied as a spray to the reproductive tissues (Cotty, supra) However, these cotton trials were conducted in Arizona where environmental factors (low relative humidity and high temperatures) may have limited the success in establishment of an aerially applied inoculant.

Due to anatomical differences between corn and either cotton or peanuts, soil inoculation may not be the most effective biological control strategy for corn. Despite the widespread use and reliable success of solid inoculants in cotton and peanuts, the strategy has not been commercially adopted for aflatoxin control in corn. Difference in the observations between soil and spray treatments in this study may be explained by the application method. While fruiting structures in peanuts are below the soil surface, a soil application is directed near the area of infection. In addition, the reproductive structures in cotton are distributed from the third to twelfth node, and are relatively close to the soil surface. By contrast, corn is a fast growing, relatively tall grass species that produces vulnerable reproductive structures greater than two meters from the soil. For colonization and subsequent displacement of indigenous aflatoxigenic strains on corn, a high level of inoculum with a consistent and uniform transfer mechanism may be required for soil applied biocontrol agents to reach and be maintained on the aerial target sites, i.e., corn ears. Whereas, in the case of a direct spray application, this requirement may be unnecessary as was demonstrated in this study. A further advantage of direct spray application of formulated K49 for commercial purposes is the ready availability of a viable stable formulation of K49 conidia.

Deposit of the Microorganisms: *Aspergillus flavus*, strain K49, designated NRRL. 30797, *Aspergillus flavus*, strain CT3, designated NRRL 30798, have been deposited under the provisions of the Budapest Treaty on Dec. 10, 2004 with the U,S.D.A, Agricultural Research Service Patent Culture Collection (National Center for Agricultural Utilization Research, 1815 N. University Street, Peoria, ILL, 61604).

The subject cultures have been deposited under conditions that assure that access to the cultures will be available during the pendency of this patent application to one determined by the Commissioner of Patents and Trademarks to be entitled thereto under 37 CFR 1,14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits wily be stored and made available to the public in accord with the provisions of the Budapest Treaty for the Deposit of Microorganisms, ie, they will be stored with all the care necessary to keep them viable and uncontaminated for a period of at least five years after the most recent request for the furnishing of a sample of the deposit, and in any case, for a period of at least 30(thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. A water-dispersible granular biocontrol formulation for administering to crop plants comprising: (1) a biocontrol agent comprising an effective amount of a conidia preparation of a non-toxigenic or non-aflatoxigenic *Aspergillus* strain for the reduction of aflatoxin contamination of food and feed commodities; (2) a binding agent; (3) an agent having osmoprotectant and adhesive properties; (4) a carrier agent, and (5) a nutrient source wherein the biocontrol agent is in suspension, wherein the amount of osmoprotectant adhesive agent is in the range of about 5-20% by dry weight of the complete formulation, wherein said agents and nutrient source exist in said formulation as a blended mixture, and wherein said biocontrol agent is embedded in a matrix of said mixture, said embedded biocontrol agent maintaining viability with a high degree of stability when upon dispersion in water and administered, is released to function biocompetitively.

2. The water-dispersible granular biocontrol agent formulation of claim 1, wherein said *Aspergillus* strain is selected from the group consisting of *Aspergillus oryzae, Aspergillus flavus, Aspergillus parasiticus, Aspergillus sojae*, and mixtures thereof.

3. The water-dispersible granular biocontrol agent formulation of claim 2, wherein said non-toxigenic *Aspergillus* strain is *Aspergillus flavus* strain K49 and said non-aflatoxigenic *Aspergillus* strain is *Aspergillus flavus* strain CT3.

4. The water-dispersible granular biocontrol agent formulation of claim 1, wherein said binding agent is sodium carboxymethylcellulose.

5. The water-dispersible granular biocontrol agent formulation of claim 4, wherein said formulation is comprised of about 4% sodium carboxymethylcellulose.

6. The water-dispersible granular biocontrol agent formulation of claim 1, wherein said osmoprotectant adhesive agent is trehalose.

7. The water-dispersible granular biocontrol agent formulation of claim 6 wherein said formulation is comprised of about 20% trehalose.

8. The water-dispersible granular biocontrol agent formulation of claim 1, wherein said carrier agent is a clay having a size comparable to the size of the conidia and of a size small enough to not lead to clogs in the sprayer system.

9. The water-dispersible granular biocontrol agent formulation of claim 8, wherein said carrier agent is a silicate clay or clay mixture.

10. The water-dispersible granular biocontrol agent formulation of claim 9, wherein said silicate clay or clay mixture is calcined kaolin, bentonite, kaolinite, or a smectite.

11. The water-dispersible granular biocontrol agent formulation of claim 10, wherein said carrier agent is calcined kaolin clay.

12. The water-dispersible granular biocontrol agent formulation of claim 11, wherein said formulation is comprised of about 75-90% calcined kaolin clay.

13. The water-dispersible granular biocontrol agent formulation of claim 10, wherein said smectite is montmorillonite or beidellite.

14. The water-dispersible granular biocontrol agent formulation of claim 1, wherein said nutrient source is trehalose.

15. The water-dispersible granular biocontrol agent formulation of claim 1, wherein said formulation is a sprayable dispersion capable of remaining in suspension with minimal agitation/stirring.

16. The formulation of claim 15 wherein said sprayable dispersion is an aqueous solution.

17. The water-dispersible granular biocontrol agent formulation of claim 1, wherein said biocontrol agent is effective when said formulation is applied at a rate of 5 to 20 kg/ha.

18. The water-dispersible granular biocontrol agent formulation of claim 1, wherein said high degree of stability is indicated by a minimal loss of viability after 11 months of storage.

19. The water-dispersible granular biocontrol agent formulation of claim 1, wherein said high degree of stability is indicated by about a 50% loss of viability after 2years of storage.

20. A method of preparing a biocontrol agent in a water-dispersible granular formulation, comprising the steps:
 (a) mixing dry ingredients comprising sodium carboxymethylcellulose, trehalose, and a silicate clay or clay mixture until visually homogeneous;
 (b) suspending an effective amount of the non-toxigenic or non-aflatoxigenic *Aspergillus* conidia in a peptone solution comprising trehalose or other known osmoprotectants/nutrients to form a conidia-containing solution; and
 (c) mixing said dry ingredients together with the conidia-containing solution to form the water-dispersible granular biocontrol formulation.

21. The method of preparing a biocontrol agent in a water-dispersible granular formulation of claim 20 wherein the silicate clay or clay mixture comprises calcined kaolin, bentonite, kaolinite, or a smectite.

22. The method of preparing a biocontrol agent in a water-dispersible granular formulation of claim 20 wherein the silicate clay or clay mixture is a calcined kaolin clay.

23. A method of preparing a biocontrol agent in a water-dispersible granular formulation, comprising the steps of claim 20 and further comprising the step of drying said formulation under vacuum to obtain vacuum-dried granules.

24. The method of claim 23 wherein the vacuum-dried granules are redispersed in water to yield a sprayable formulation.

25. The method of claim 24 wherein the vacuum-dried granules are redispersed in water to yield a sprayable formulation comprising 0.2-2.0% granules (w/v).

26. The method of claim 20 wherein the water-dispersible granular biocontrol formulation is a stable formulation capable of maintaining $10^8$-$10^9$ CFUs/g after extended periods of storage.

27. The method of claim 20 wherein the water-dispersible granular biocontrol formulation is a stable formulation of a biological control agent that maintains its phenotype and its characteristic of aggressive colonization of crops after extended periods of storage.

28. A method for reducing aflatoxin contamination of food and feed commodities comprising applying to said commodities, a biocontrol formulation prepared by the process of:
 (a) mixing dry ingredients comprising sodium carboxymethylcellulose, trehalose, and a silicate clay or clay mixture until visually homogeneous:
 (b, suspending an effective amount of the non-toxigenic or non-aflatoxigenic *Aspergillus* conidia in a peptone solution comprising trehalose to form a conidia-containing solution; and
 mixing said dry ingredients together with the conidia-containing solution to form the water-dispersible granular biocontrol formulation.

29. The method or reducing aflatoxin contamination of food and feed commodities of claim 28 wherein the silicate clay or clay mixture comprises calcined kaolin bentonite, kaolinite, or a smectite.

30. The method for reducing aflatoxin contamination of food and feed commodities of claim 29 wherein the silicate clay or clay mixture is a calcined kaolin clay.

31. The method of any one of claims 28-30 wherein said commodities are selected from the group consisting of peanuts, corn, cottonseed, cereal grains, olives, and tree nuts.

* * * * *